United States Patent
Herrmann et al.

(10) Patent No.: US 9,266,711 B2
(45) Date of Patent: Feb. 23, 2016

(54) INSPECTION DEVICE FOR INSPECTING FOREIGN MATTER

(75) Inventors: Jürgen Herrmann, Rosenheim (DE); Claas Fritsche, Dortmund (DE); Marius Michael Herrmann, Rosenheim (DE); Alfred Drenguis, Börnsen (DE)

(73) Assignee: KHS GmbH, Dortmund (DE)

( * ) Notice: Subject to any disclaimer, the term of this patent is extended or adjusted under 35 U.S.C. 154(b) by 341 days.

(21) Appl. No.: 13/990,565

(22) PCT Filed: Nov. 8, 2011

(86) PCT No.: PCT/EP2011/005595
§ 371 (c)(1),
(2), (4) Date: May 30, 2013

(87) PCT Pub. No.: WO2012/076089
PCT Pub. Date: Jun. 14, 2012

(65) Prior Publication Data
US 2013/0233437 A1    Sep. 12, 2013

(30) Foreign Application Priority Data

Dec. 8, 2010    (DE) .......................... 10 2010 053 772

(51) Int. Cl.
| | |
|---|---|
| *B67C 3/00* | (2006.01) |
| *B67D 7/32* | (2010.01) |
| *B67C 3/24* | (2006.01) |
| *G01N 29/04* | (2006.01) |
| *G01N 29/22* | (2006.01) |

(52) U.S. Cl.
CPC .............. *B67D 7/3281* (2013.01); *B67C 3/007* (2013.01); *B67C 3/24* (2013.01); *G01N 29/046* (2013.01); *G01N 29/225* (2013.01); *G01N 2291/2695* (2013.01)

(58) Field of Classification Search
CPC .......... B67C 3/24; B67C 3/242; B67C 3/007; G01N 29/046; G01N 29/225; G01N 2291/2695
USPC .................................. 141/2, 83, 94, 165, 372
See application file for complete search history.

(56) References Cited

U.S. PATENT DOCUMENTS

| | | | |
|---|---|---|---|
| 3,608,715 A | * | 9/1971 | Snyder et al. ................. 209/590 |
| 4,184,372 A | | 1/1980 | Brown |
| 5,880,359 A | * | 3/1999 | Kono et al. .................... 73/49.3 |

(Continued)

FOREIGN PATENT DOCUMENTS

| | | |
|---|---|---|
| CN | 1276865 | 12/2000 |
| DE | 202 17 559 | 1/2003 |
| DE | 202 18 138 | 4/2004 |
| DE | 102 57 238 | 6/2004 |

(Continued)

*Primary Examiner* — Timothy L Maust
*Assistant Examiner* — Timothy P Kelly
(74) *Attorney, Agent, or Firm* — Occhiuti & Rohlicek LLP

(57) ABSTRACT

A container handling installation in which retaining and transport elements transport containers in a transport direction and in which filling stations fill containers with product includes an inspection device for checking the container for unwanted foreign matter. The inspection device is integral with the retaining and transport element and includes a piezo sensor. Also included is an evaluation unit connected to the inspection device. The inspection device is configured to connect to the container such that the container and the inspection device move together in a respective direction of movement and in the transport direction.

10 Claims, 3 Drawing Sheets

(56) References Cited

U.S. PATENT DOCUMENTS

| | | | |
|---|---|---|---|
| 6,782,752 B2* | 8/2004 | Basir et al. | 73/625 |
| 2012/0012224 A1* | 1/2012 | Haeuslmann | 141/1 |
| 2013/0248321 A1* | 9/2013 | Herrmann et al. | 198/339.1 |
| 2014/0216142 A1* | 8/2014 | Fiegler | 73/61.75 |

FOREIGN PATENT DOCUMENTS

| | | |
|---|---|---|
| DE | 10 2004 051 961 | 5/2006 |
| DE | 10 2006 048 327 | 4/2008 |
| GB | 2 189 320 | 10/1987 |
| WO | WO 03/029806 | 4/2003 |

* cited by examiner

INSPECTION DEVICE FOR INSPECTING FOREIGN MATTER

CROSS REFERENCE TO RELATED APPLICATION

This application is the national phase under 35 USC 371 of international application no. PCT/EP2011/005595, filed Nov. 8, 2011, which claims the benefit of the priority date of German application no. 10 2010 053 772.1, filed Dec. 8, 2010. The contents of the aforementioned applications are incorporated herein in their entirety.

FIELD OF DISCLOSURE

The invention relates to a container handling installation, in particular a filling machine, in which containers such as bottles or similar and also cans are transported in a transport direction by means of retaining and transport elements, and in which respective containers are filled with a product at filling stations, wherein the container handling installation has at least one inspection device for checking bottles or similar containers for unwanted foreign matter, said inspection device being connected to an evaluation unit.

BACKGROUND

Such bottles or similar containers can be used for fluids, for example drinks. The containers can be made of a transparent or translucent material, for example glass, or a translucent plastic, e.g. PET.

It is known to inspect such containers for unwanted foreign matter in the filled product by means of an inspection device, not only for reasons of consumer health but if such foreign matter is found, it can ruin the reputation of the product manufacturer concerned. Therefore such a foreign matter inspection is performed with great care in order e.g. to prevent possible product liability claims.

Such foreign matter inspections can be carried out with optical inspection devices as disclosed e.g. in DE 102 57 238 A1 or devices based on X-ray radiation (for example DE 202 17 559 U1; DE 10 2006 048 327 A1; DE 202 18 138 U1).

These systems which function well in principle however have their limits if the containers to be inspected are very dark or even opaque, such as for example metal cans, or if the product is very cloudy and/or contains solids or fibres.

An inspection method is also known in which a piezo sensor is used under laboratory conditions as disclosed in AiF Report 264 ZBG (Novel multicontact detection as a basis for an innovative hybrid system for automatic detection of particulate solid foreign bodies in filled, flowable, non-lumpy foodstuffs on the example of products of selected rheological constitution; Delgado, Antonio; Benning, Rainer; Forstner, Judith; Erlangen; FAU Erlangen-Nürnberg, 2009 (AIF264ZBG)).

The procedure disclosed in AIF264ZBG is intended to be suitable for detecting foreign bodies in fluids by means of signal reception by the piezo sensor and vibration analysis after excitation of the fluid. The containers used for the tests performed were 0.5 liter bottles as used for beer or soft drinks. For the digital simulation by means of the finite element method (ANSYS CFX simulation software), for example a bottle filled with water was selected in order to investigate whether a translational or a rotational acceleration is most suitable for positioning. The foreign bodies were substantially spherical glass particles with diameters 0.5 mm, 1.0 mm and 1.5 mm. In addition theoretical tests were first performed with PET particles but also with olive oil. The clamping force can be set in a defined manner by the adjustability of the upper bottle centring and the sprung mounting of the base. The latter also achieves a comparatively simple implementation of the necessary decoupling from vibrations acting from the outside. The signal reception by the piezo sensor takes place exclusively via the base of the bottle in that the piezo sensor is glued directly onto the base of the bottle.

In principle in this way foreign matter can also be detected in containers and/or products which are difficult to inspect. However the findings of the report are based solely on laboratory measurements.

SUMMARY

The invention is based on the object of improving a container handling installation, in particular a filling machine, of the type cited initially, or its inspection device, with simple means such that foreign matter can be detected more reliably.

According to the invention this object is achieved by a container handling installation, in which the inspection device is designed as an integral component of the retaining and transport element and as a piezo sensor, wherein the inspection device can be connected with the container such that this can be moved along the transport direction together with the inspection device.

The invention is based on a container handling installation which can be designed in rotating circulation or with a linear transporter, wherein the retaining and transport element can comprise a gripper section for holding the containers. Usually the container handling installation has several retaining and transport elements, i.e. a number of retaining and transport elements corresponding to the number of treatment stations. For example, the container handling installation is designed as a filling machine so that a number of retaining and transport elements corresponding to the number of filling stations is provided.

The transport direction in the sense of the invention is the direction in which the container is supplied to the individual successive treatment stations and/or possible inspection stations, wherein a movement direction—which will be defined below—is generated independently of the transport direction. The movement direction can be about the vertical axis of the container but also along this, or at an angle thereto, also in each case overlaid. It is favourable if the at least one inspection device is always connected with the container both in the transport direction but also in the optional movement direction.

When product is filled in the container, the product has a relative speed to the container itself. This is where the invention is used. For example, foreign matter present in the container before filling and not yet detected can be flushed by the inflowing product and thus, because of the movement of the product, impact on the inner wall of the container. It is however also conceivable that unwanted foreign matter is contained in the product to be filled, which because of the product movement within the container can also impact on its inner wall. This impact pulse from unwanted foreign matter impacting on the inner wall is received by the inspection device or the piezo sensor and supplied to the evaluation unit, which thus generates a decision signal for the container to remain in the production line or be rejected. The evaluation unit is naturally designed such that these signals from unwanted foreign matter can be distinguished from signals from desirable solids.

The invention provides a container handling installation and an inspection device which can reliably detect foreign matter inside the container or in the filled product.

In a suitable embodiment it can be provided that the at least one piezo sensor is arranged in the gripper segment of the retaining and transport element.

It is possible that the gripper segment has a form adapted to the holding segment of the container, wherein the piezo sensor in a particularly suitable embodiment is also integrated in the gripper segment adapted to the holding segment, preferably on its inner region.

In a particularly preferred embodiment, the inspection device or piezo sensor always has contact with the container to be inspected so that the impact pulses via the wall of the container and the measurement region concerned of the retaining and transport element can be received by the piezo sensor arranged there.

It is conceivable that in the material of the retaining and transport element is provided a recess i.e. as a window corresponding to the form of the piezo sensor, so that the piezo sensor with its measurement region can have direct contact with the container to be inspected. It is also possible to integrate the piezo sensor or its measurement region below a protective layer in the retaining and transport element so that an indirect but adequate measurement contact can be achieved with the container to be inspected.

Using the piezo sensor, unwanted foreign matter in the product can be detected reliably, wherein an external excitation of the container up to a fluid relative speed is not absolutely necessary. Furthermore the inspection device can also provide a double function. It is conceivable that the inspection device, at the same time as the foreign matter inspection, can monitor the filling quantity, i.e. the inspection device can also determine a weight. Advantageously in addition a further piezo sensor for weight measurement can be arranged on or integrated in the retaining and transport element. In a favourable embodiment the piezo sensor is integrated on an arm segment of the retaining and transport element oriented radially to the container. Evidently the evaluation unit is also adapted to this weight function.

In the invention it is suitable to design the piezo sensor as an integral part of the retaining and transport element so that the inspection device is arranged on the container handling installation itself, and a connection to the container to be inspected with the inspection device can be created very quickly but also detachably at will, without the inspection device having to be attached by substance fit i.e. glued to the container in order to carry out a foreign matter inspection.

On the retaining and transport element, at its connection to the container handling installation, a corresponding connection can be provided for wireless transmission of power and data to and from the piezo sensor. For energy supply however also an internal energy source can be used which can be arranged on the retaining and transport element. For data transmission also a transmitter can be provided which allows a wireless transmission to a receiver which in turn can be connected wirelessly or hardwired with the evaluation unit.

As already stated, no excitation of the container is required. However it is evidently conceivable to excite the container to a movement which is independent of the transport movement along the transport direction. The retaining and transport element can for example comprise a movement point on which an excitation element acts. For example the excitation element could provoke a reciprocating movement of the container along or transverse to its vertical axis so that the product in the container is excited to a movement, wherein also unwanted foreign matter or desirable solids can impact on the inner wall. It is also possible to excite a rotation of the product in the container e.g. by overlaying both movements previously mentioned. By means of an excitation element the container can thus be excited to a movement which can be stopped abruptly or also reversed. Due to the mass inertia of the filled product, this moves or can rotate, wherein possible unwanted foreign bodies impact on the inner wall of the container, wherein this signal is received by the piezo sensor which naturally also receives signals from desirable solids and passes these to the evaluation unit.

It is suitable if one or more piezo sensors are arranged on the retaining and transport element or are integral parts thereof, wherein at least one piezo sensor is an integral part of least one of each retaining and transport element in order to carry out an inspection for unwanted foreign matter at the same time as filling.

It is also possible for the container to stand on a plate and be held at the head side by means of the retaining and transport element. It is also possible to clamp the container along the vertical axis of the container by means of the retaining and transport element on the head side and the plate. The retaining and transport element can thus have the function of holding, wherein the plate together with the retaining and transport element performs the transport in the transport direction. Suitably the at least one inspection device can hence also be an integral part of the plate. In the simplest embodiment the plate with the piezo sensor integrated therein can easily be placed on the base side of the container so that the necessary contact is created. It is also possible to arrange carrier elements on the plate integrating the least one inspection device in the embodiment as a piezo sensor.

Carrier elements can also be provided which extend away from the standing surface of the plate, and the main webs of which carrying the piezo sensors lie spring-like against the container outer wall. Naturally in particular the regions of the main web which comprise the piezo sensors lie against the container. Evidently the carrier elements can have different or the same longitudinal extensions.

In a further embodiment the carrier elements can not only be arranged rigidly on the plate but also be movable from a rest position to an inspection position and back. For this suitable drives can be used, for example electric motor or pneumatic drives, which move the carrier elements along the vertical axis of the container to be inspected. The carrier element with its measurement region, i.e. the region in which the piezo sensor is arranged, can be moved from below against the base of the container or passed by the base and laid on a body region of the container, which naturally also applies to the movable carrier elements on the head-side retaining and transport element. The plate can also have a rotary drive to excite the container to rotation for example. The energy supply for the drive of the rotary drive, the carrier element and/or the piezo sensor can be integrated in the plate or the retaining and transport element or be external. The external energy supply not only to the carrier elements but also to the piezo sensors can take place as in known turntables e.g. via a slip ring, an inductive transmitter (RFID) and/or by means of dynamo supply. Also a hardwired or wireless signal transmission from the least one piezo sensor to the evaluation unit is possible.

It is however also conceivable that the at least one piezo sensor is integrated in the plate itself. For this it can be provided that the plate comprises at least one carrier layer and a sensor layer, i.e. can be constructed of at least two layers. Thus it is possible to arrange the bottle carrier layer radially on the outside, and provide the sensor layer on the inside, i.e. centrally in the middle. Carrier materials can be metals, glass, ceramics, gels, gel cushions, fluids of suitable type and/or technical fabrics. Naturally also a multilayer construction is possible. It is also conceivable to cast the piezo sensor or sensors in the plate or in its metal base plate. It is however also essential here that the piezo sensor or sensors have contact with the container surface in order to be able to receive the impact signals.

The analysis unit can combine amplifier, computer, converter and or filter elements and also be designed as a type of control unit.

Advantageously the invention also provides a method for inspection of containers with an inspection device in one of the embodiments described above, wherein the method comprises at least the following steps:
- holding of the container in the transport direction by means of the retaining and transport element;
- filling of the container with a product;
- contacting of at least one piezo sensor with the container, wherein the piezo sensor is an integral part of at least the retaining and transport element;
- receiving of signals from the particles impacting on the inner wall of the container by means of the at least one piezo sensor when the container is or has been filled with the product; and
- transmission of the signals received by the at least one inspection device to an evaluation unit which detects a decision with regard to whether the container contains foreign matter or non-foreign matter.

It is possible at the same time as the foreign matter inspection to also carry out a weight check with regard to the necessary quantity filled. This function can be performed by the at least one inspection device, wherein naturally also a further piezo sensor can be designed for weight measurement. In principle however it is possible in the sense of the invention to carry out a weight measurement together with the foreign matter detection.

In particular excitation of the container to movement after filling can also be provided, which can be repeated in order to achieve a fluid movement within the container so that unwanted foreign matter can impact on the container inner wall. Thus a type of monitoring inspection for foreign matter can be performed.

Evidently several data sets from several piezo sensors can be received and evaluated simultaneously. The excitation to movement can take place similarly i.e. constantly, although a pulse-like excitation is also conceivable. It is also possible as already stated to overlay the vertical and horizontal movement directions, i.e. as a type of vibrational excitation of the container to be inspected.

BRIEF DESCRIPTION OF THE FIGURES

Further advantageous embodiments of the invention are disclosed in the sub claims and in the figure description below. This shows:

DETAILED DESCRIPTION

Figure 1:
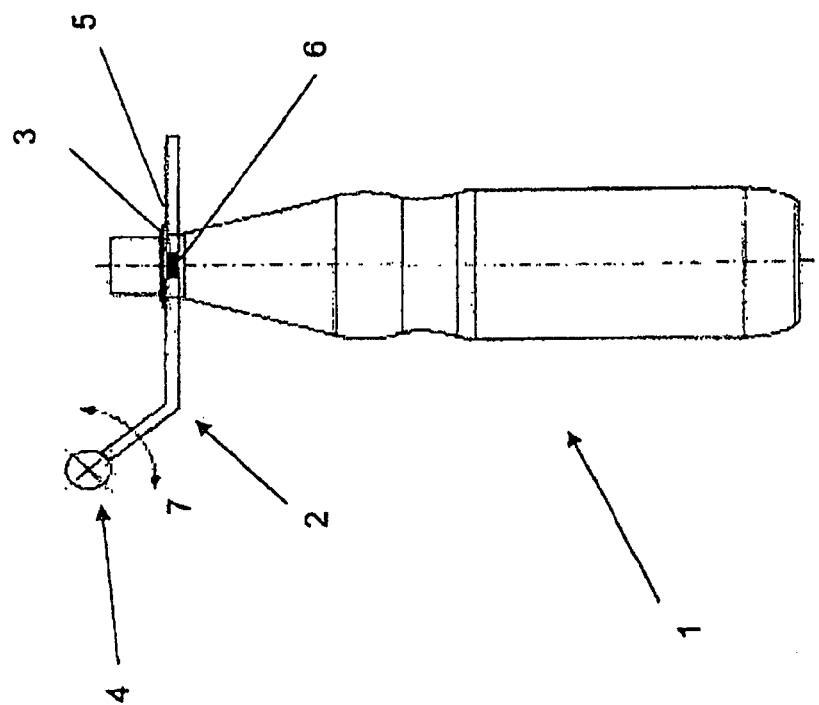
FIG. 1 a retaining and transport element of a container handling installation as a detail, FIG. 2 a container clamped between a retaining and transport element on the head side and a plate on the foot side, FIG. 3 a plate as a detail in a possible embodiment with carrier elements.

In the different figures, the same parts always carry the same reference numerals so these are usually only described once.

FIG. 1 shows a container 1 which can be inspected in a container handling installation not shown further. The container handling installation is preferably a filling machine which fills the containers 1 with a product. For this a multiplicity of filling stations is provided along a rotationally circulating or linear transport direction. Depending on the number of container treatment stations, the container handling installation has a corresponding or equal number of retaining and transport elements 2. As shown in FIG. 1, these grip on a mouth region of the container 1 at a neck ring 3 as shown.

The retaining and transport element 2 has a connecting point 4 for the container handling installation, wherein a gripper segment 5 is arranged opposite. With the gripper segment 5, the retaining and transport element 2 can grip the container 1. For this the gripper segment 5 is preferably adapted to the embodiment of the associated segment of the container 1.

FIG. 1 does not show any filling elements. The product to be filled enters the container 1 through the filling elements.

At the container handling installation is provided at least one inspection device 6 for foreign matter inspection. According to the invention the at least one inspection device 6 is an integral part of the retaining and transport element 2 and is designed as a piezo sensor 6.

Favourably at least one piezo sensor 6 is an integral part of each retaining and transport element 2.

According to the preferred embodiment example in FIG. 1, the at least one piezo sensor 6 is an integral part of the gripper segment 5 of the retaining and transport element 2.

On filling of the product, by means of the at least one piezo sensor 6, impact contacts of unwanted foreign matter on the inner wall of the container 1 can be received and transmitted to an evaluation unit not shown. Naturally also impact contacts of desirable solids on the inner wall are received and transferred to the evaluation unit. The evaluation unit is advantageously designed so that it can distinguish the impact contacts of unwanted foreign matter from those of desirable solids, and can generate a decision signal for the retention or rejection of the container 1 inspected.

As the products to be filled in principle have a relative speed to the container interior, the unwanted foreign matter and/or the desirable solids are excited sufficiently for impact contact on the container inner wall to be possible. To this extent external excitation can be virtually avoided but is still possible.

For the external excitation of the container 1, excitation elements can be provided which can be located for example at the connecting point 4, as indicated by the movement arrow 7.

In this way the container 1 can be excited to movement during or after filling, which can cause impact contacts of said substances on the inner wall.

At the same time as the foreign matter inspection, it is also possible to carry out an inspection of the filled product quantity, which signals are also passed to the evaluation unit. To this extent it is possible with the at least one piezo sensor 6 to carry out not only a foreign matter inspection but also a weight measurement. Naturally it is conceivable to carry out both inspections with different piezo sensors which are however arranged on one and the same retaining and transport element 2, which is useful. The additional piezo sensor for weight measurement can however be arranged on an arm segment of the retaining and transport element 2 pointing radially to the container 1. Naturally this inspection device for weight measurement need not necessarily be designed as a piezo sensor but can assume any another form.

Figure 2:
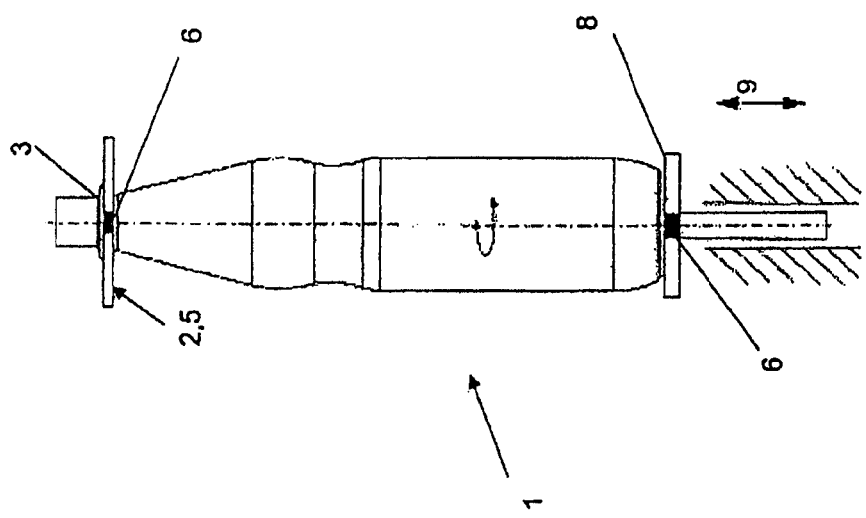

In a further possible embodiment the container 1 on the foot side can stand on a plate 8 and on the head side be guided by a retaining and transport element 2 (FIG. 2). The plate 8 is movable in the height direction (double arrow 9) so that the container 1 can be held clamp-like when the retaining and transport element 2 and the plate 8 make corresponding contact.

As shown in FIG. 2, the inspection device 6 or the piezo sensor 6 can be an integral part of the plate 8. The plate 8 with the integral piezo sensor 6 can be moved against the base of the container 1 in order to receive the impact signals.

It is possible to design the plate in two layers with a carrier layer and a sensor layer, or even in multiple layers.

Figure 3:
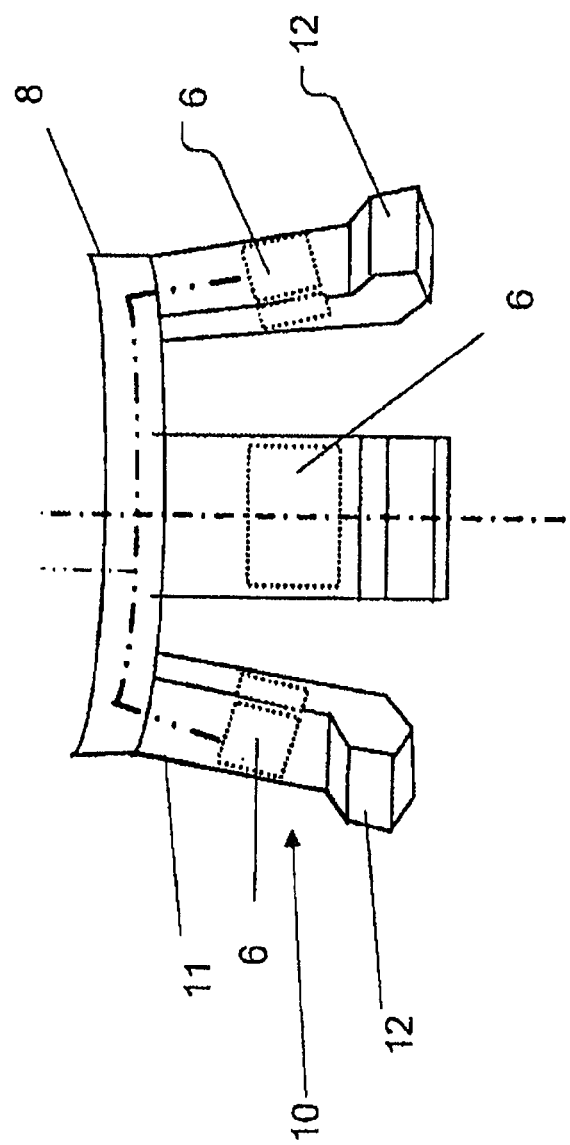

It is however also conceivable to arrange at least one carrier element 10 on the plate 8 in which the piezo sensor 6 is integrated, as shown in FIG. 3. FIG. 3 also shows the standing surface of the plate 8 oriented towards the lower edge of the page, wherein several carrier elements 10 provided evenly distributed about the periphery.

The respective carrier element 10 extends with its main web 11 oriented away from the standing surface of the plate 8 in the direction towards the retaining and transport element 2. At one free end of the main web 11 is arranged a foot web 12. To this extent it can be said that the carrier element 10 is designed quasi L-shaped.

The piezo sensor 6 is preferably arranged in the respective main web 11. Favourably the main web 11 is designed such that at least with its measurement region it can lie under a quasi spring force against the container 1 standing on the plate 8. The measurement region is defined by the position of the piezo sensor 6.

It is possible to design the individual carrier elements 10 with different longitudinal extensions so the different contact regions on the container 1 can be reached.

It is also conceivable to arrange the carrier elements 10 not rigidly on the plate 8 but movable. Thus the carrier elements 10 or the piezo sensors 6 integrated therein can reach any arbitrary measurement region of the container 1.

As indicated in FIG. 3, a hardwired or wireless connection can exist from the individual piezo sensors 6 to the evaluation unit. A transmitter can also be provided on the plate 8 which is connected with a receiver.

Similarly to the design of the carrier elements 10 on the plate 8, it is naturally also conceivable to provide such carrier elements 10 on the retaining and transport element 2 or on the filler element itself.

It is suitable in the sense of the invention to provide, as an inspection device for internal inspection of the container 1 for unwanted foreign matter, at least one inspection device 6 in the embodiment of the piezo sensor 6 which is preferably designed as an integral part of the retaining and transport element 2 and/or the plate 8.

By means of the plate 8, the container 1 can also be excited in a movement direction additional to the transport direction. The transport direction in the sense of the invention is the direction in which the container is supplied to the individual successive filling stations, wherein the movement direction is generated independently of the transport direction. Thus the movement direction can be about the vertical axis of the container 1 as shown in FIG. 2, but also along this or at an angle thereto, also in each case overlaid, as indicated in FIG. 1.

Preferably by means of a rotation drive, a rotary movement of the container 1 about its vertical axis is generated, for which the plate 8 with its rotary drive is best suited as this can generate rotation speeds of more than 1000 rpm. To this extent the plate 8 is not only a support and orientation element but also has the function of an excitation element for movement excitation of the container 1.

The inspection device 6, in an advantageous embodiment as the piezo sensor 6, is able to detect unwanted foreign matter in products in which e.g. an optical method would meet its limits.

In the embodiment example shown in FIG. 3, all carrier elements 10 have the same longitudinal extension. It is also possible to design the respective carrier elements 10 with different longitudinal extensions. Thus at least one piezo sensor 6 can e.g. lie on a body region of the container 1, wherein at least one other can be arranged in its mouth region. It is conceivable to design each carrier element 10 mobile in its longitudinal extension so that virtually any desired region of the container 1 can be measured individually with the piezo sensor 6. For this the carrier elements 10 can be moved from a rest position into an arbitrary measurement or inspection position.

Naturally the at least one piezo sensor can be arranged not only on the example filling machine but also on labelling machines, closing machines and similar container handling installations. This container handling installations can be designed as a rotating transport device or as linear conveyors. In linear conveyors at least one piezo sensor 6 can be integrated in the retaining and transport element in the design as a conveyor belt.

Also an embodiment is possible in which the piezo sensor measures contactless.

The invention claimed is:

1. An apparatus comprising
a container-handling installation,
wherein said container-handling installation comprises
a plurality of retaining-and-transport elements, and
a plurality of filling stations,
wherein said plurality of retaining-and-transport elements comprises a first retaining-and-transport element,
wherein said plurality of filling stations comprises a first filling-station,
wherein said first filling-station fills containers with product,
wherein said first retaining-and-transport element transports containers in a transport direction,
wherein said first retaining-and-transport element comprises an inspection device,
wherein said inspection device comprises a piezo sensor,
wherein said inspection device is configured for checking said container for unwanted foreign-matter,
wherein said inspection device is integral with said first retaining-and-transport element,
wherein said inspection device provides data for evaluation,
wherein said inspection device is configured to connect to said container such that said container and said inspection device move together in a respective direction of movement and in said transport direction, and
wherein said inspection device is integral with a gripper segment of a retaining-and-transport element.

2. The apparatus of claim 1, wherein said inspection device is an integral part of each retaining-and-transport element of said container handling installation.

3. The apparatus of claim 1, wherein said inspection device is configured to connect to a side-wall region of said container.

4. The apparatus of claim 1, wherein said inspection device is integral with a plate for engaging a foot side of said container.

5. The apparatus of claim 1, wherein said inspection device is integral with a carrier element.

6. The apparatus of claim 1, further comprising a plurality of carrier elements, each of which is associated with a corresponding one of said retaining-and-transport elements, wherein said plurality of carrier elements comprises a first carrier element, wherein said first carrier element is arranged to move between a rest position and an inspection position on said first retaining-and-transport element and/or on a plate on a foot side, wherein said inspection device is integral with said carrier element.

7. A method for internal inspection of containers in a container-handling installation having a filling machine that includes retaining-and-transport elements that transport containers in a transport direction and filling stations that fill containers with product, said retaining-and-transport elements comprising a first retaining-and-transport element, said container-handling installation comprising a first inspection device for checking said container for unwanted foreign-matter, wherein said first inspection device is integral with said first retaining-and-transport element, wherein said first inspection device includes a piezo sensor that is integral with said first retaining-and-transport element, wherein said first inspection device provides data for evaluation, wherein said first inspection device is configured to connect to said container such that said container and said first inspection device move together in a respective direction of movement and in said transport direction, said method comprising executing a foreign-matter inspection, wherein executing a foreign-matter inspection comprises holding a container in said transport direction, element,
filling said container with a product,
causing said container and said first piezo sensor to come into connect during filling of said container,
receiving a signal indicative of particular pressure waves arising from foreign matter impacting on an inner wall of said container when said container is filled with said product and/or immediately thereafter,
transmitting said signal for evaluation to determine whether to regard said container as containing foreign matter, and
wherein said method further comprises using said piezo sensor to perform a weight check concurrently with executing said foreign-matter inspection.

8. The method of claim 7, further comprising causing said container to move, wherein causing said container to move comprises promoting a likelihood that said foreign matter will impact said inner wall.

9. The method of claim 7, further comprising concurrently receiving a first dataset from said first inspection device and a second data set from a second inspection device.

10. An apparatus comprising
a container-handling installation comprising
retaining-and-transport elements, and
a plurality of filling stations,
wherein said retaining-and-transport elements comprise a first retaining-and-transport element,
wherein said plurality of filling stations comprises a first filling station,
wherein said first filling station fills containers with product,
wherein said first retaining-and-transport element transports containers in a transport direction,
wherein said first retaining-and-transport element comprises a rotation drive,
wherein said first retaining-and-transport element comprises an inspection device,
wherein said inspection device comprises a piezo sensor,
wherein said inspection device is configured for checking said container for unwanted foreign-matter,
wherein said inspection device is integral with said first retaining-and-transport element,
wherein said inspection device provides data for evaluation,
wherein said inspection device is configured to connect to said container such that said container and said inspection device move together in a respective direction of movement and in said transport direction,
wherein said inspection device is integral with a plate for engaging a foot side of said container, and
wherein said rotation drive causes rotary movement of said container about a vertical axis thereof.

* * * * *